(12) United States Patent
Lesniak et al.

(10) Patent No.: US 10,723,051 B2
(45) Date of Patent: *Jul. 28, 2020

(54) AIR FRESHENER

(71) Applicant: Brandywine Product Group International, Inc., Wilmington, DE (US)

(72) Inventors: Frank M. Lesniak, Media, PA (US); Kyle Brandenburg, Middletown, DE (US); John R. Hickman, North Canton, OH (US)

(73) Assignee: Brandywine Product Group International, Inc., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/458,757

(22) Filed: Jul. 1, 2019

(65) Prior Publication Data

US 2019/0358877 A1 Nov. 28, 2019

Related U.S. Application Data

(60) Continuation of application No. 15/263,523, filed on Sep. 13, 2016, now Pat. No. 10,369,731, which is a
(Continued)

(51) Int. Cl.
*B29C 45/16* (2006.01)
*A61L 9/04* (2006.01)
(Continued)

(52) U.S. Cl.
CPC .......... *B29C 45/16* (2013.01); *A01M 1/2055* (2013.01); *A01M 29/12* (2013.01);
(Continued)

(58) Field of Classification Search
CPC ... A61L 9/04; A61L 9/12; A61L 9/048; A61L 2209/15; A01M 31/008; A01M 1/2055;
(Continued)

(56) References Cited

U.S. PATENT DOCUMENTS

| 2,816,323 A | 12/1957 | Munger |
| 3,733,016 A | 5/1973 | Rood |

(Continued)

FOREIGN PATENT DOCUMENTS

CA 2183030 A 2/1998

*Primary Examiner* — Steven J Ganey
(74) *Attorney, Agent, or Firm* — Rogowski Law LLC

(57) ABSTRACT

An air freshener has a rigidifying core defining a central axis, and an outer portion or sleeve contacting the core that is formed from one or more fragrance loaded polymers. Together, the core and outer portion are shaped to surround a first axis perpendicular to the central axis. The air freshener is made by injection molding a first shot of at least one polymer material to form the core, and injection molding a second shot of at least one polymer material incorporating one or more fragrance materials over or onto or into at least a portion of the core. The second shot of polymer material may be stretched about the portion of the core during injection molding, and may flow into a first hole formed in the core at or near the core distal end, and fills a second hole formed in the core at or near the core proximal end.

15 Claims, 10 Drawing Sheets

Related U.S. Application Data division of application No. 14/788,924, filed on Jul. 1, 2015, now Pat. No. 9,474,821, which is a continuation of application No. 13/491,814, filed on Jun. 8, 2012, now Pat. No. 9,107,969.

(51) Int. Cl.

| | | |
|---|---|---|
| *A01M 29/12* | (2011.01) | |
| *A01M 1/20* | (2006.01) | |
| *A01M 31/00* | (2006.01) | |
| *A44C 15/00* | (2006.01) | |
| *B29C 45/00* | (2006.01) | |
| *A61L 9/12* | (2006.01) | |
| *B29C 45/18* | (2006.01) | |
| *B29C 45/27* | (2006.01) | |
| *B29C 45/28* | (2006.01) | |
| *B29L 9/00* | (2006.01) | |

(52) U.S. Cl.
CPC ......... *A01M 31/008* (2013.01); *A44C 15/002* (2013.01); *A61L 9/04* (2013.01); *A61L 9/048* (2013.01); *A61L 9/12* (2013.01); *B29C 45/0001* (2013.01); *B29C 45/0003* (2013.01); *B29C 45/1866* (2013.01); *B29C 45/2737* (2013.01); *B29C 45/28* (2013.01); *A61L 2209/15* (2013.01); *B29K 2995/0037* (2013.01); *B29L 2009/00* (2013.01)

(58) Field of Classification Search
CPC ...... A01M 29/12; A44C 15/002; B05B 15/00; B29C 45/0003; B29C 45/16; B29C 45/0001; B29C 45/1866; B29C 45/2737; B29C 45/28; B29K 2995/0037; B29L 2009/00

USPC ................................ 239/34, 36, 57, 60, 289

See application file for complete search history.

(56) References Cited

U.S. PATENT DOCUMENTS

| | | | |
|---|---|---|---|
| 4,735,626 | A | 4/1988 | Smith |
| D301,912 | S | 6/1989 | Ward |
| 5,013,513 | A | 5/1991 | Schad |
| 5,374,178 | A | 12/1994 | Nakayama |
| 5,407,642 | A | 4/1995 | Lord |
| 5,468,447 | A | 11/1995 | Bermas |
| 5,527,493 | A | 6/1996 | McElfresh et al. |
| 5,697,665 | A | 12/1997 | Itou |
| 5,865,372 | A | 2/1999 | Ceresko |
| 5,899,382 | A | 5/1999 | Hayes et al. |
| 6,149,038 | A | 11/2000 | Tsai |
| 6,264,887 | B1 | 7/2001 | Farmer |
| D485,341 | S | 1/2004 | Wu |
| D518,162 | S | 3/2006 | Miro |
| D531,039 | S | 10/2006 | Couey |
| 7,182,270 | B2 | 2/2007 | Buthier |
| D540,932 | S | 4/2007 | Burgeson |
| D553,730 | S | 10/2007 | Wu |
| D594,337 | S | 6/2009 | Burgeson |
| 7,687,038 | B2 | 3/2010 | Wheatley et al. |
| D648,430 | S | 11/2011 | Short et al. |
| 8,685,330 | B2 * | 4/2014 | Irvin .................. A61L 9/042 422/120 |
| 9,107,969 | B2 * | 8/2015 | Lesniak .................. A61L 9/12 |
| 2004/0109916 | A1 | 6/2004 | Babin |
| 2005/0199740 | A1 | 9/2005 | Harris |
| 2011/0108632 | A1 | 5/2011 | Brandenburg et al. |
| 2011/0215167 | A1 | 9/2011 | Boyd |
| 2012/0315317 | A1 | 12/2012 | O'Hara |

\* cited by examiner

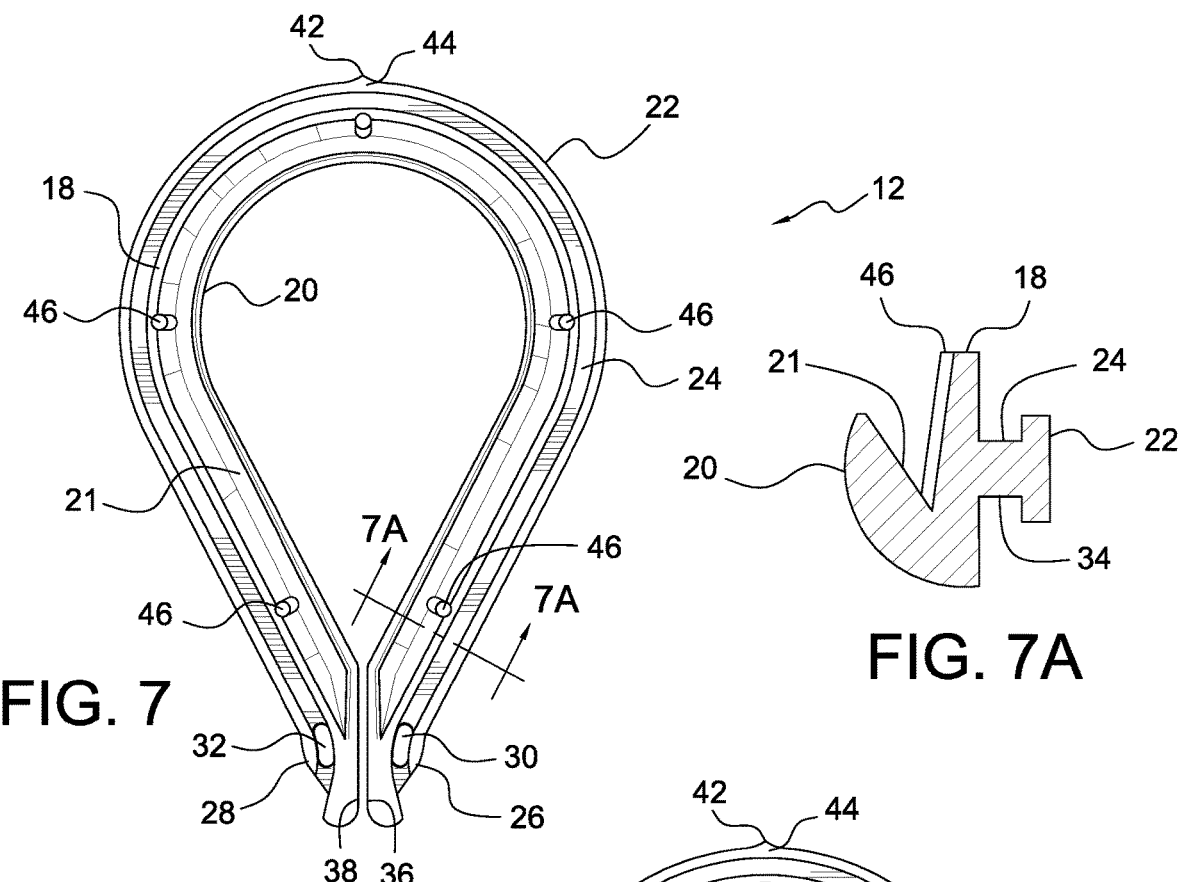
FIG. 7
FIG. 7A
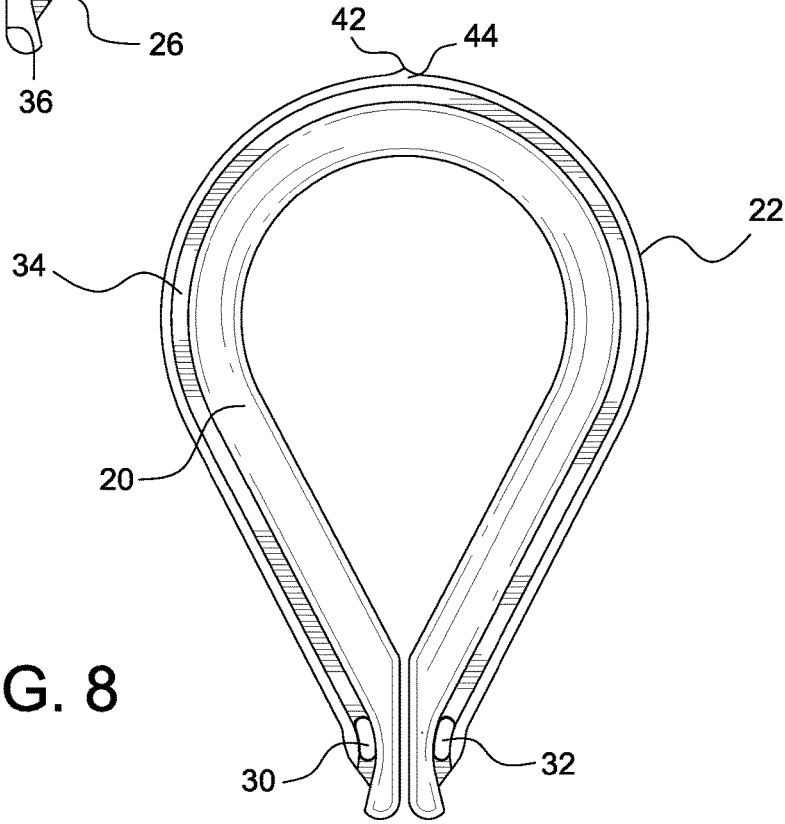
FIG. 8

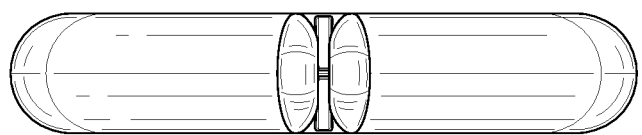
FIG. 12
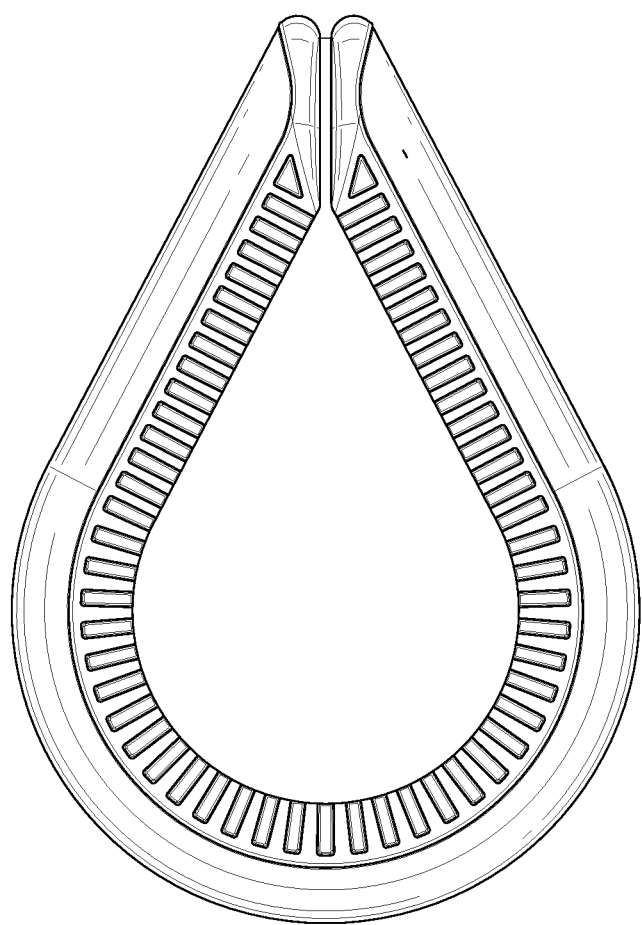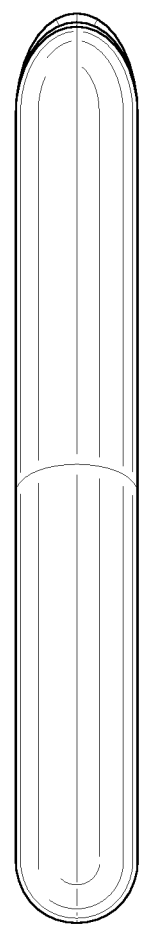
FIG. 11  FIG. 14
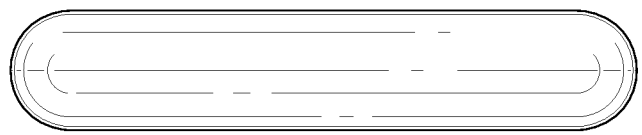
FIG. 13

AIR FRESHENER

CROSS-REFERENCE TO RELATED APPLICATIONS

This application is a continuation of U.S. patent application Ser. No. 15/263,523, filed Sep. 13, 2016, which is a divisional of U.S. patent application Ser. No. 14/788,924, filed Jul. 1, 2015, now U.S. Pat. No. 9,474,821, which was a continuation of Ser. No. 13/491,814, filed Jun. 8, 2012, now U.S. Pat. No. 9,107,969.

FIELD OF THE INVENTION

The present invention relates to an air freshener formed of one or more polymer resin(s) and having at least one portion or sleeve loaded with a fragrance oil or oils or other fragrance material. The air freshener may be formed as a clip with a strengthening core onto which the outer portion may be over molded. Opposing ends of the air freshener are juxtaposed adjacent to one another when the air freshener is in closed position. The opposing ends of the air freshener may be urged apart or flexed apart to open the air freshener for installation over or around a receiving structure. The air freshener is adapted to be hung around rods, handles or arms, such as, but not limited to, the neck or shoulder of an automotive rear view mirror, to be suspended therefrom and release fragrance into the air.

BACKGROUND OF THE INVENTION

The passenger compartments of automobiles and trucks may retain unpleasant odors introduced into such compartment by drivers, passengers or cargo. Examples of unpleasant odors include cigarette and cigar smoke, food odors, body odors, retained cargo odors and gas or exhaust fumes. Various air freshener devices have been designed for use in vehicle passenger compartments, including devices that suspend from a rear view mirror or from a sun visor.

Effective continuous action air fresheners release a sufficient amount of fragrance such that for a given enclosed space, such as a room or a motor vehicle passenger compartment, the fragrance is readily perceptible when someone enters that space. In addition effective air fresheners deliver fragrance for an acceptable period of time, such as 30 to 60 days. Moreover, such air fresheners should maintain fragrance character over this time period, such that the odor impression of the fragrance when the air freshener is activated as compared to the fragrance character at the end of the functional life is relatively the same.

Air freshening clips that join to the fins of automotive or household venting systems are shown in the prior art. See, e.g., U.S. Pat. Nos. 5,407,642; 5,527,493; 5,865,372; 6,264,887; and 7,687,038. Other representative hanging or suspending air freshener devices include charms or novelty devices hung by string or stretchable elastic yarns, or air freshening devices suspended by hooks. See, e.g., U.S. Pat. Nos. 7,182,270 and 5,468,447. Scent emitting clothes hangers are also known. See, e.g., U.S. Pat. No. 6,149,038.

Consumers may prefer portable air freshener devices that may be installed quickly and removed quickly from living spaces and motor vehicle passenger compartments. Devices that may be moved from one location to another location easily also are preferred. Consumers further may prefer air freshener devices with outer configurations that more discretely fit within a living space or motor vehicle passenger compartment.

Improvements to air freshener devices for use in conjunction with small spaces, such as motor vehicle passenger compartments, closets and storage areas, continue to be sought.

SUMMARY OF THE INVENTION

In a first aspect, an air freshener has a core defining a proximal end, a distal end, a length between the proximal end and distal end, and a central axis along the length of said core of the air freshener. The air freshener further has a fragranced polymer sleeve contacting at least a portion of the core. The fragranced polymer sleeve comprises at least one polymer incorporating one or more fragrances. The fragranced polymer sleeve may be over-molded over a portion of the core. In closed position, the air freshener may encircle an axis that is substantially perpendicular to the central axis. The proximal end and the distal end may be close to one another when the air freshener clip is in a closed configuration. The proximal end and the distal end are spaced apart by flexing or moving apart when the air freshener is in an open configuration, and preferably return to substantially their closed position after flexing. The proximal end may terminate at a face and the distal end may terminate at a second face, and the face and second face may be juxtaposed in substantially facing relation to one another when the air freshener is in closed configuration. The face and second face may contact one another or may be spaced apart from one another when the air freshener is in closed configuration. With these configurations, the air freshener may form a clip for attachment to a receiving structure. In one embodiment, the face surface of the proximal end and the second face surface of the distal end are adapted for removable connection to one another. In another embodiment, a strap joins the proximal end and the distal end together. Such strap maintains the proximal end and distal end in close proximity, and is broken or cut to permit separation of the ends when installing the air freshener around a receiving structure.

The core may be formed of a polymer selected from the group consisting of: polyvinylchloride, polyethylene, polyethylene terephthalate (PET), polyoxymethylene (Delrin), polyamide (nylon), low density polyethylene (LDPE), high density polyethylene (HDPE), polypropylene, ethylene vinyl acetate, acrylonitrile butadiene styrene (ABS), styrene-acrylonitrile (SAN), rubber, thermoplastic elastomer (TPE), silicone, copolymers thereof, and mixtures thereof. The fragranced polymer is formed of a polymer selected from the group consisting of: polyvinylchloride, polyethylene, low density polyethylene (LDPE), high density polyethylene (HDPE), thermoplastic elastomer (TPE), polypropylene, ethylene vinyl acetate, ELVAX® EVA ethylene vinyl acetate copolymer, acetate, butyrate, propionate, silicone, copolymers thereof, and mixtures thereof. The core polymer and the fragranced polymer may be selected such that the polymer materials chemically bind or adhere to one another. Alternatively, the core polymer and the fragranced polymer may be selected such that the polymer materials do not bind to one another, to allow the fragranced polymer to slip or move in relation to the core polymer at the interface between the core polymer and the fragranced polymer.

In some embodiments, both the core polymer and the fragranced polymer sleeve incorporate or contain one or more fragrance oils. Fragrance oils may be natural or synthetic, or combinations of such.

In another embodiment of the invention, an air freshener comprises a core defining a proximal end, a distal end, a length between the proximal end and distal end, and a central axis along the length of said core of the air freshener, and a sleeve contacting at least a portion of the core, where the sleeve comprises at least one polymer incorporating one or more fragrances. The air freshener surrounds or encircles an axis that is substantially perpendicular to the central axis. The central axis may be curved along at least a portion thereof. The sleeve may be over-molded over a portion of the core.

The core may have an upstanding inner wall beginning at or near the proximal end and terminating at or near the distal end of the air freshener. The core also may define a first trough between a first side of the upstanding inner wall and an inside exterior wall. The core also may have an I-beam strengthening section spaced apart from the upstanding inner wall and having an upper I-beam wall generally following the contour of said upstanding inner wall. The upstanding inner wall and I-beam strengthening section of the core may define a second trough therebetween. The I-beam strengthening section may terminate at one end defining a hole between the I-beam strengthening section and the distal end of the air freshener. The I-beam strengthening section may terminate at its other end defining a second hole between the I-beam strengthening section and the proximal end of the air freshener. The core may further define a third trough between the inside exterior wall and the I-beam strengthening section. The I-beam strengthening section may define an apex and a reinforcement may be provided at such apex, to stabilize or reinforce the clip for repeated bending and flexing. Preferably, the sleeve is disposed over and around the I-beam strengthening section, and through the first hole and second hole of the I-beam strengthening section. The sleeve material may also be disposed in the second trough and the third trough, where the sleeve abuts one side of the upstanding inner wall and one side of the inside exterior wall of the core.

In some embodiments, the face surface of the proximal end and the second face surface of the distal end abut one another. The face surface of the proximal end and the second face surface of the distal end also may be adapted for removable connection to one another. For example, a male connector may extend from at least one of the face surface of the proximal end and the second face surface of the distal end, and a female connector may be defined by the other of the at least one of the face surface of the proximal end and the second face surface of the distal end. The male connector may be received within the female connector for linking engagement to close the air freshener around a receiving structure. The male connector may be released from the female connector to permit the proximal end and distal end to be separated apart, and thereby to release the air freshener clip from a receiving structure. As another example, the face surface of the proximal end may define a cavity or recess to receive the distal end of the air freshener. In such configuration, distal end of the air freshener may have an outer diameter that is smaller than the outer diameter of the proximal end of the air freshener.

In yet another embodiment, an air freshener may have a core defining a proximal end, a distal end and a central axis of the air freshener, where the air freshener encircles an axis that is substantially perpendicular to the central axis. The core may have an upstanding inner wall beginning at or near the proximal end and terminating at or near the distal end of the air freshener. In this embodiment, the core further may have an interior section defining a plurality of ribbed channels between a first side of the upstanding inner wall and an inside exterior wall. A sleeve may contact at least a portion of the core, said sleeve comprising at least one polymer incorporating one or more fragrances. The sleeve may be over-molded over the core. The proximal end and the distal end of the air freshener are separable from one another and movable (or flexed) away from one another, either in a direction generally parallel to said axis that is substantially perpendicular to the central axis, or in a direction along the central axis, or in a combination of such directions. Preferably, the core is formed of a polymer material without fragrance oil. When viewed in cross section, the core preferably comprises more than 180° of the exterior periphery of the air freshener. This embodiment may include the I-beam strengthening section, and the sleeve may be disposed over and around such I-beam strengthening section. The I-beam strengthening section may include a reinforcement at the apex of the air freshener.

The air freshener of still another embodiment of the invention may indicate the level of fragrance dissipation. In this embodiment, the outer portion or sleeve overmolded over the core is not molded around straps or through holes provided at or near the distal and proximal ends of the air freshener. After passage of a predetermined time, with the dissipation of the fragrance oil from the polymer of the outer portion or sleeve, the sleeve length shrinks to a length that is less than its initial sleeve length (determined immediately after the sleeve is installed or over-molded onto the core). This shrinkage will be observed by an ordinary observer because greater portions of the core at the distal end and at the proximal end of the air freshener previously covered by the outer portion or sleeve will be exposed to view.

One possible method for making an air freshener includes the steps of: (1) injection molding a first shot of at least one polymer material to form a core, said core defining a proximal end, a distal end and a central axis of the air freshener; and (2) injection molding a second shot of at least one polymer material incorporating one or more fragrance materials onto or into or over at least a portion of the core. The second shot may form a sleeve over at least a portion of the core. Preferably, injection molding is conducted in a valve gated hot runner system. Preferably, the sleeve is disposed over and around an I-beam strengthening section formed in the core. In a particularly preferred embodiment, the second shot of polymer material is stretched about the core during injection molding.

The method for making an air freshener is particularly suitable for making an air freshener that has a core with an upstanding inner wall beginning at or near the proximal end and terminating at or near the distal end of the air freshener. The core further may define a first trough between a first side of the upstanding inner wall and an inside exterior wall. The I-beam strengthening section may be spaced apart from the upstanding inner wall and have an upper I-beam wall generally following the contour of said upstanding inner wall. The upstanding inner wall and I-beam strengthening section may define a second trough therebetween. Preferably, the I-beam strengthening section terminates at one end defining a hole between the I-beam strengthening section and the distal end of the air freshener, and terminates at its other end defining a second hole between the I-beam strengthening section and the proximal end of the air freshener. The core still further may define a third trough between the inside exterior wall and the I-beam strengthening section. With this air freshener structure, it is possible for the second shot of polymer material to flow into and fill the first hole and second hole of the I-beam strengthening section.

This helps stabilize the second shot of polymer material onto and in connection with the core, and lessens shrinkage where shrinkage is not desired.

A method of emitting fragrance into a small space, such as an automobile passenger compartment or a closet or other small space, comprises installing an air freshener clip according to the invention onto or around a receiving structure. Possible receiving structures include, but are not limited to, rear view mirrors, rear view mirror supports or necks, motor vehicle door handles, curtain rods, closet rods, hangers, shelving, shelving support posts, drawer pulls, drawer handles, belt loops, shoes, shoe racks, hampers, gym bags, lockers, shower doors, towel racks, trash cans, pipes, wires, tables and carts.

DESCRIPTION OF THE FIGURES

Numerous other objects, features and advantages of the invention shall become apparent upon reading the following detailed description taken in conjunction with the accompanying drawings, in which:

FIG. 7 is a rear plan view of a core of an air freshener;

FIG. 7A is a cross-sectional view of the core taken along line 7A-7A in FIG. 7;

FIG. 8 is a front plan view of the core of FIG. 7;

FIG. 11 is a front plan view of the air freshener of FIG. 9;

FIG. 12 is a bottom view of the air freshener of FIG. 9;

FIG. 13 is a top view of the air freshener of FIG. 9;

FIG. 14 is a right side view of the air freshener of FIG. 9;

DESCRIPTION OF THE PREFERRED EMBODIMENTS

Figure 1:
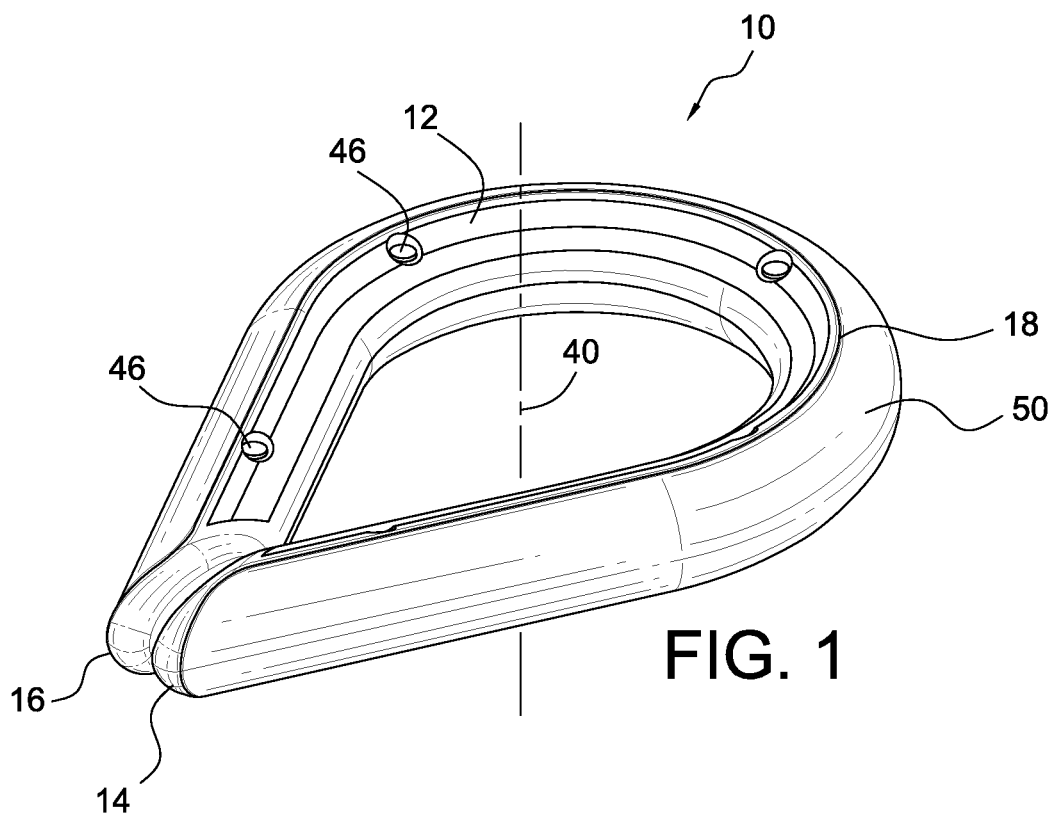
FIG. 1 is a right rear perspective view of an air freshener.

With reference to the drawings in which like numerals designate similar elements, a first embodiment of an air freshener 10 is shown in FIGS. 1-6. The air freshener 10 is comprised of a central core 12 with an outer portion or sleeve 50. The core 12 is shown more particularly in FIGS. 7 and 8. The air freshener 10 has a proximal end 14 and a distal end 16, and is looped or curved or rounded about an axis 40 to form a round or teardrop shape. The air freshener 10 preferably has at least a portion that is curved, such as shown in FIGS. 1-6. Alternatively, the air freshener 10 may encircle or surround the axis 40 with other polymeric or geometric or regular or irregular shape.

In a preferred embodiment, the proximal end 14 and distal end 16 of the air freshener 10 have generally planar face surfaces 36, 38 that are juxtaposed in slightly spaced apart, facing relationship. However, all or some portions of the planar faces 36, 38 of each of the proximal end 14 and distal end 16 may abut or contact one another when the air freshener 10 is in its closed configuration. The air freshener 10 may form a clip, such that in its closed configuration it can be clipped to a receiving structure or mounting structure.

Referring to FIGS. 7 and 8, the core 12 of this embodiment has an upstanding inner wall 18 that extends from the proximal end 14 to the distal end 16 and generally follows the curved or shaped contour of the air freshener 10. Mold gating locations 46 are shown adjacent the upstanding inner wall 18. The upstanding inner wall 18 is spaced apart from an inside exterior wall 20 defining a trough 21 therebetween. The inner trough walls formed by the upstanding inner wall 18 and inside exterior wall 20 may be generally straight, or may be angled. Preferably, the exterior of the inside exterior wall 20 is convexly curved.

The upstanding inner wall 18 of the air freshener 10 of the embodiment of FIGS. 7 and 8 is spaced apart from an I-beam strength section 22 defining a second trough 24 therebetween. The inner trough walls of the second trough formed by the upstanding inner wall 18 and the I-beam strength section 22 may be generally straight, as shown in FIG. 7, or may be angled. As shown in FIG. 7, the trough 24 has a generally planar lower trough surface. The I-beam strength section 22 generally follows the curved or shaped contour of the air freshener 10 and the upstanding inner wall 18. The I-beam strength section 22 has an outer wall that terminates near the distal end of the air freshener. Strap 26 joins the end of the I-beam strength section 22 to the proximal end 14 of the air freshener 10. Second strap 28 joins the opposite end of the I-beam strength section 22 to the distal end 16 of the air freshener 10. Between the strap 26 and the upstanding inner wall 18 a hole 30 is formed. Between the second strap 28 and the upstanding inner wall 18 a hole 32 is formed. The holes 30, 32 may be oval slots, or other desired hole configuration.

The air freshener 10 defines a central axis along its length. Where the air freshener 10 is curved, such central axis is curved, and the air freshener 10 may form a curved shape, such as in the configuration of a tear drop as shown in FIGS. 1-6.

The I-beam strength section 22 of the core 12 may have a reinforcement 44 at the apex 42 of the curved I-beam strength section 22. As shown in FIGS. 7 and 8, the reinforcement 44 comprises an added amount of material thickness in the "I" portion of the I-beam strength section, thus reinforcing the core 12 to accommodate bending stresses when the proximal end 14 and distal end 16 of the air freshener 10 are flexed apart or moved away from one another to open the air freshener.

Figure 2:
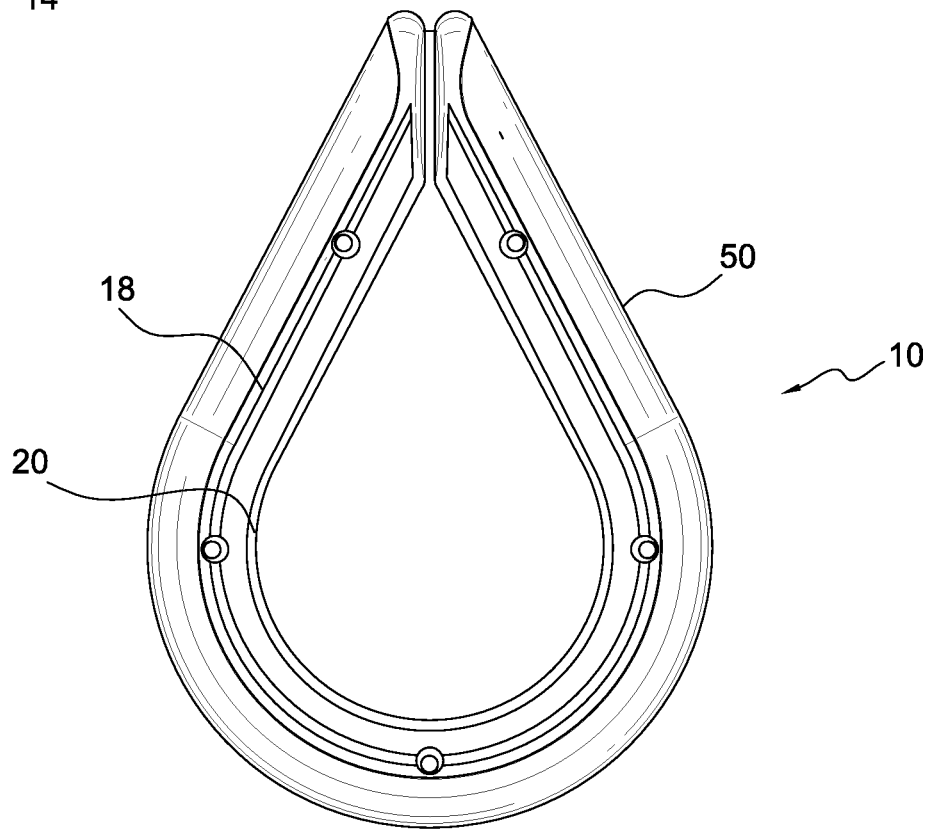
FIG. 2 is a rear plan view of the air freshener of FIG. 1.
Figure 4:
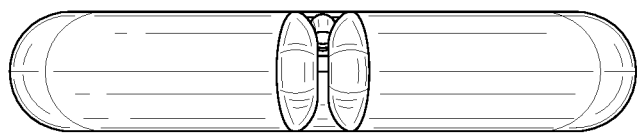
FIG. 4 is a bottom view of the air freshener of FIG. 1.
Figure 3:
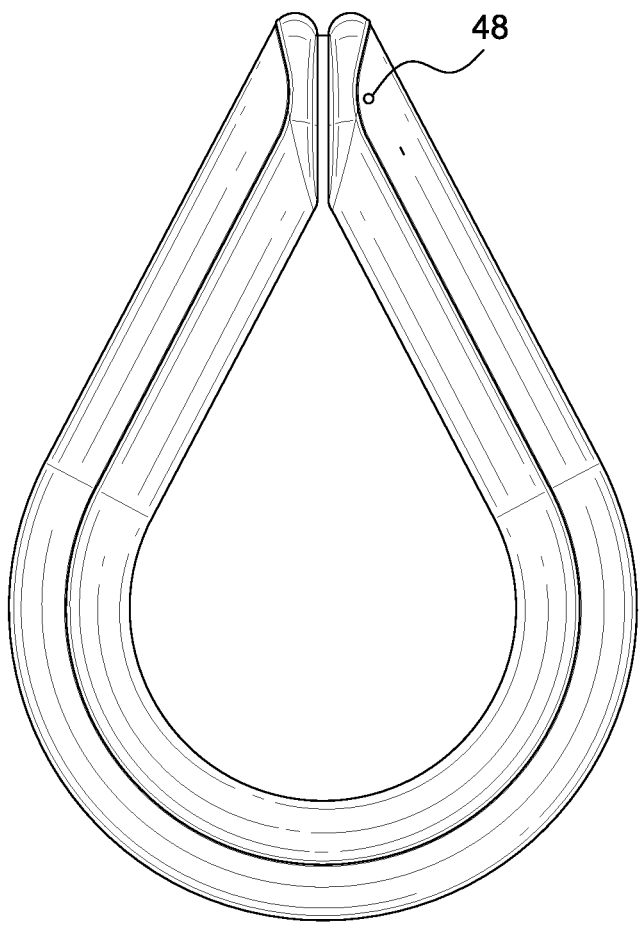
FIG. 3 is a front plan view of the air freshener of FIG. 1.
Figure 6:
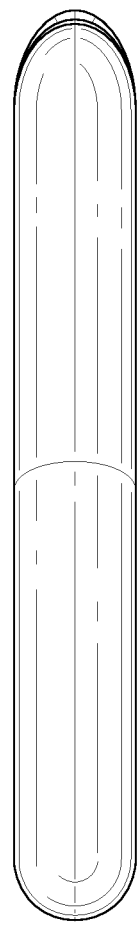
FIG. 6 is a right side view of the air freshener of FIG. 1.
Figure 5:
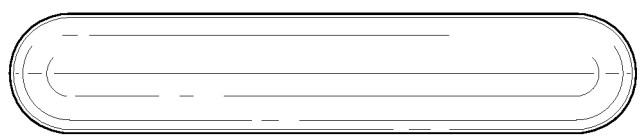
FIG. 5 is a top view of the air freshener of FIG. 1.
Figure 9:
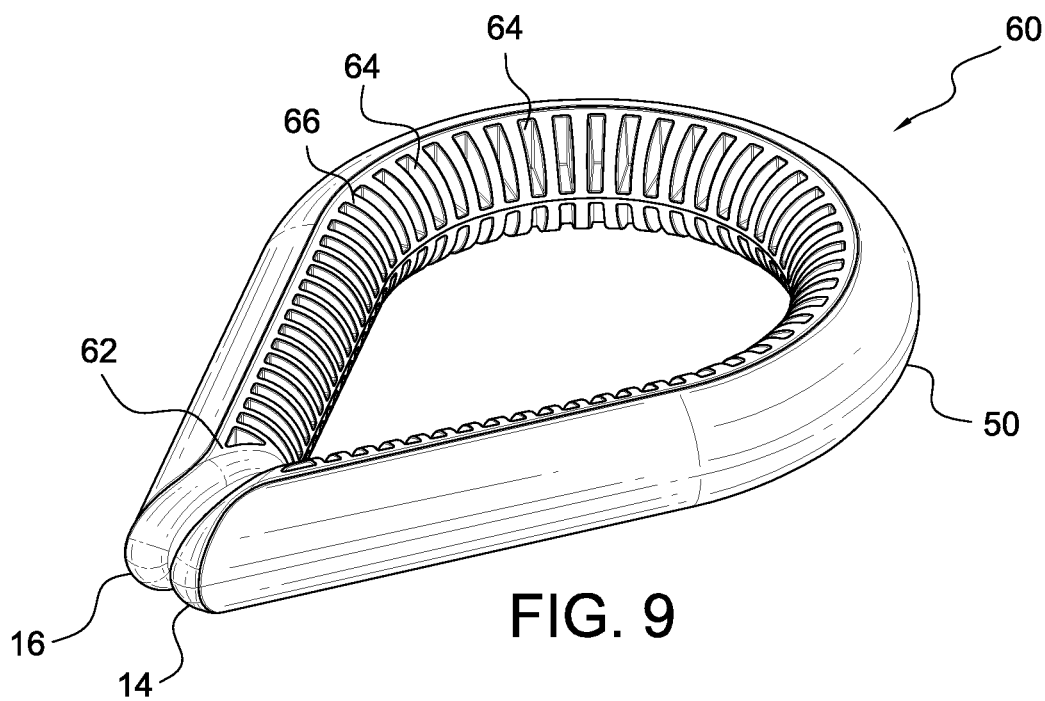
FIG. 9 is a right rear perspective view of an alternative air freshener.
Figure 10:
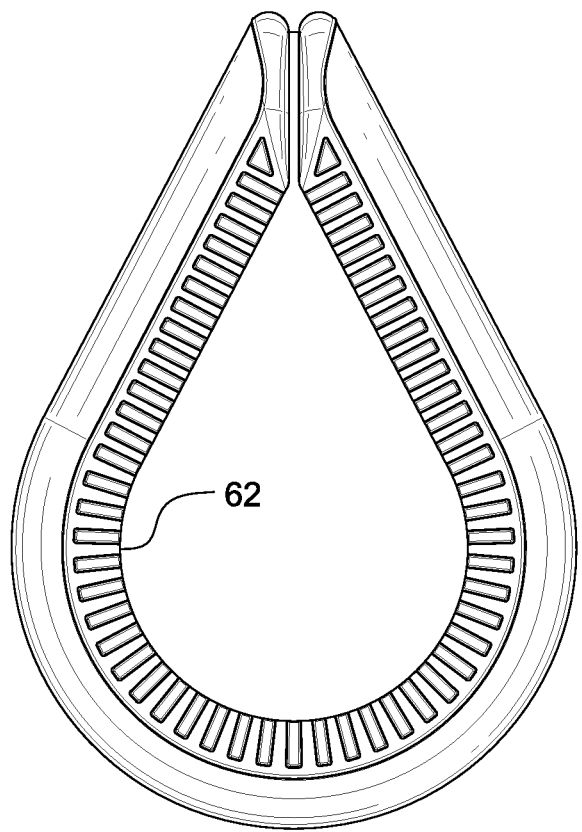
FIG. 10 is a rear plan view of the air freshener of FIG. 9.

In this embodiment, an outer portion or sleeve 50 of fragranced polymer or fragranced polymer mixture is molded over (or over-molded over) a portion of the core 12. As shown in FIGS. 1 and 2, the sleeve 50 abuts one side of the upstanding inner wall 18, and fills the second trough 24. The sleeve material covers the I-beam strength section 22 and fills the third trough 34. Preferably, the sleeve material is not molded into the first trough 21. The sleeve 50 preferably is molded to have a convexly curved outer surface. Upon molding, the sleeve material covers the straps 26, 28 that join the ends of the I-beam strength section 22 to the proximal and distal ends of the air freshener, and the sleeve material flows into the holes 30, 32, thus securing the sleeve material to the proximal and distal ends of the air freshener 10 and to the I-beam strength section.

Alternatively, the I-beam strength section 22 may terminate at each end without having straps 26 and without forming the holes 30, 32. The outer portion or sleeve material (fragranced polymer or polymer mixture) may be over-molded over the core 12, in the same manner, but without locking around straps or into holes. In such embodiment, the sleeve material functions also to indicate when fragrance has depleted from the air freshener 10. The sleeve material shrinks as fragrance dissipates from the sleeve material polymer. Such shrinkage will be evident first at the proximal and distal ends of the air freshener, where the sleeve material may begin to pull away from such ends. In such embodiment, it is preferable that fragranced polymer outer portion 50 comprises a polymer or mixture of polymers different from that comprising the core 12, and the polymer materials do not chemically bind to one another and are not otherwise adhered to one another to permit the desired shrinkage or slippage.

The core 12 may be molded from a polymer containing at least one resin selected from the group consisting of: polyvinylchlorides (PVC), polyethylenes (PE), polyethylene terephthalates (PET), polyoxymethylene (Delrin), polyamides (nylon), low density polyethylene (LDPE), high density polyethylene (HDPE), polypropylenes, ethylene vinyl acetate, acrylonitrile butadiene styrene (ABS), and styrene-acrylonitrile (SAN), rubber, thermoplastic elastomer (TPE), silicone, copolymers thereof and mixtures thereof. The resin composition may be mixed, blended or compounded together optionally with additives known in the art and with one or more fragrance materials to form an injection-moldable mixture before injection molding. A preferred amount of resin to form the core is from 2 g to 100 g, more preferably 3 g to 20 g.

The outer portion or sleeve 50 may be a different polymer resin from that selected for the body or core 12. The sleeve 50 may be over molded over the core 12 in a multiple shot molding process. In a multiple shot molding process, the core 12 is formed in a first molding step and the sleeve 50 is formed over the core 12 in a second or subsequent molding step. The core 12 and sleeve 50 may be molded by injection molding, particularly by valve gated hot runner injection molding as described in more detail below.

The fragranced polymer or outer portion or sleeve 50 may be molded from at least one resin selected from the group consisting of: polyvinylchlorides (PVC), polyethylenes (PE), high density polyethylenes (HDPE), low density polyethylene (LDPE), polyvinylchoride (PVC), polypropylenes, ethylene vinyl acetate copolymers (EVA), such as ELVAX® EVA ethylene vinyl acetate copolymer, thermoplastic elastomers (TPE), polypropylenes, acetate, butyrate and propionate, silicone, copolymers thereof, and mixtures thereof. The resin composition may be mixed, blended or compounded together with one or more fragrance materials and optionally with other additives known to those in the art to form an injection-moldable mixture before injection molding. A preferred amount of resin to form the fragranced polymer or outer portion or sleeve is from 2 g to 100 g, more preferably 3 to 20 g.

A "fragrance material" may be any material that has a smell or odor. Most conventional fragrance materials are highly volatile essential oils. Even those which are less volatile contain highly volatile "top note" fractions which preferably are retained in the composition during processing to obtain desired fragrance power and olfactory impact by the resultant molded article. A fragrance material or a combination of fragrance materials that is compatible with the selected resin composition is preferred. The fragrance material may be a synthetically formed material or may be a naturally derived oil such as, but not limited to, the oil of Bergamot, Bitter Orange, Caraway, Cedar Leaf, Cedar Wood, Champacc, Cinnamon, Frankincense, Geranium, Lavender, Mimosa, Orange, Orignaum, Patchouli, Rosewood, Sandalwood, Vanilla, Violet, White Cedar, Ylang Ylang, Limonene, menthol, eucalyptus, camphor or the like. The particular essential oil or combination of oils to be used depends upon the particular fragrance desired for emission by the product formed.

Alternatively or additionally, the fragrance material may comprise or act as a volatile insecticide and/or insecticidal synergist or attractant or repellant, such as pyrethrum, octenol, linalool, mint oil, or a bacteriostat or pheromone. Alternatively or additionally, the fragrance material may comprise or act as a vaporous remedy for respiratory conditions, such as a vapor to relieve symptoms of colds and allergies.

Available fragrance materials are catalogued and described in references and databases known to persons skilled in the art. For example, a database is maintained by the Research Institute for Fragrance Materials at www.rifm.org. Fragrance material suppliers include Takasago International Corp. (Rockleigh, N.J.) and Symrise (Teterboro, N.J.). Exemplary synthetic fragrance materials are described in U.S. Pat. Nos. 4,411,829; 4,314,915 and 4,434,306. Preferred amounts of fragrance loading in resin are from about 5% to about 45% by weight of the resin.

Colorants (such as pigments known for use with thermoplastic and thermoset resins) may be incorporated into the polymers to improve aesthetics. Examples of suitable colorants also include any water-based colorant such as food coloring, and Reactint polymeric colorant from Milliken Chemical (Spartanburg, S.C.).

Other additives may be incorporated into the polymers as desired, including one or more plasticizers, one or more stabilizers, and optionally one or more lubricants.

Preferably, the outer portion or sleeve 50 comprises a fragranced polymer that is loaded with a suitable amount of fragrance oil(s). More frequently, the polymer(s) forming the core 12 will not include fragrance oil(s). When the air freshener 10 is installed over a retaining structure, the core will contact the retaining structure surfaces. Preferably, when viewed in cross section, the core 12 comprises more than 180° of the exterior periphery of the air freshener 10. As such, only the core will contact the retaining structure surfaces. Then, such core 12 without fragrance oil(s) will not leach or dissipate fragrance oils onto the retaining structure surfaces. In some embodiments, however, the core 12 also may comprise a fragranced polymer that is loaded with a suitable amount of the same or different fragrance oil(s).

Figure 15:
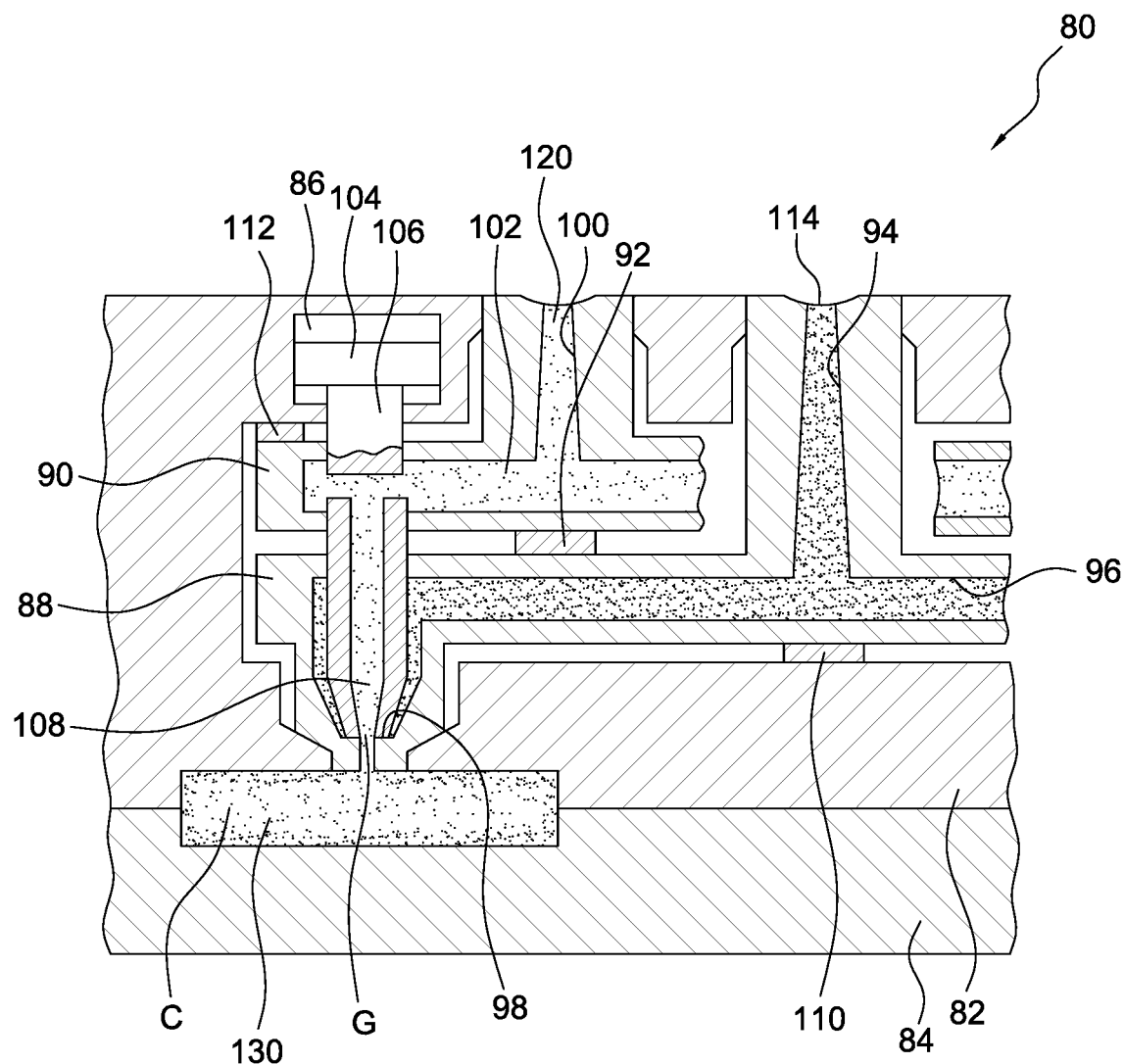
FIG. 15 is a schematic view in cross section of a valve gated hot runner system injection mold.

FIG. 15 shows a representative injection mold system 80 having a valve gated hot runner system. In FIG. 15, a fixed mold 82 and a movable mold 84 are placed in contact with each other at a mold parting surface so as to define a cavity C, a cylinder chamber 86 is formed in the fixed mold 82. A first hot runner block 88 and a second hot runner block 90 are fitted in the fixed mold 82. The first hot runner block 88 and the second hot runner block 90 are spaced a predetermined distance from each other by a heat-insulating member 92 in overlapping relation to each other. The first hot runner block 88 has a first sprue 94, a first hot runner 96, a seat portion 98, and a gate G. The second hot runner block 90 has a second sprue 100 and a second hot runner 102. A piston 104 is mounted within the cylinder chamber 86 of the fixed mold 82. A valve member 106 connected to this piston extends through the second hot runner block 90 and fits in the first hot runner block 88. A resin passage 108 is formed in the valve member 106. One end of the resin passage 108 communicates with the second hot runner 102 and the other end thereof communicates with the gate G.

When the distal end of the valve member 106 is pressed against the seat portion 98 of the first hot runner block 88 as shown in FIG. 15, the valve member is disposed in a first hot runner-closing position, the communication between the first hot runner 96 and the cavity C is interrupted. When the valve member 106 is spaced apart from the seat position, the first hot runner 96 communicates with the cavity C. Regardless of the position of the valve member 106, the second sprue 100 always communicates with the cavity C via the second hot runner 102 and the resin passage 108. A heat-insulating member 110 is provided between the fixed mold 82 and the first hot runner block 88, and a heat-insulating member 112 is provided between the fixed mold and the second hot runner block 90. The heat-insulating members 92, 110, and 112 prevent heat transfer between the first and second hot runner blocks 88 and 90, between the fixed mold 82 and the first hot runner block 88, and between the fixed mold 82 and the second hot runner block 90, respectively.

The two molds 82 and 84 are closed and clamped together by a mold clamping device (not shown). Air pressure is supplied to a lower chamber of the cylinder chamber 86 of the fixed mold 82 so as to move the valve member 106 to the first hot runner-opening position which is somewhat above the illustrated position of the valve member. By doing so, the first hot runner 96 communicates with the cavity C. A first polymer shot 114 is then injected from the first sprue 94. The first polymer shot resin 114 passes through the first sprue 94, the first hot runner 96, and the gate G, and flows into the cavity C. The injection molding is carried out at a temperature above the Vicat softening temperature of the resin, and generally above 100° C., and under pressures commonly used in injection molding.

When a predetermined amount of resin 114 has been injected, air pressure is supplied to an upper chamber of the cylinder chamber 86 so as to move the valve member 106 to the first hot runner-closing position. By doing so, the injection of the first polymer shot resin 114 is terminated. Slightly before, or simultaneously with, the end of the injection of the first polymer shot resin 114, a second shot polymer resin 120 is injected from the second sprue 100. The second shot polymer resin 120 passes through the second sprue 100, the second hot runner 102, and the gate C, and finally flows into the cavity C. After a predetermined amount of the second shot resin 120 has been injected, the process is finished. Accordingly, a molded product 130 having a core of second polymer and a sleeve of first polymer can be produced. Since the second shot polymer resin 120 can be injected successively after the injection of the first shot polymer resin 114, or vice versa, the resin flow never stops, and therefore, hesitation marks are not likely to develop on the surface of the molded product.

The I-beam strengthening section 22 of the core 12 of the preferred embodiment air freshener 10 allows the second shot forming the outer portion or sleeve 50 to slide between the two attached ends to reduce internal stresses and reduce total part warpage.

The gating locations 46 on the first shot polymer resin forming the core and the gating location 48 on the second shot polymer resin forming the sleeve are intended to use molecular orientation to help reduce total part warpage by better dimensional control as the air freshener 10 is injection molded.

Referring next to FIGS. 9 to 14, an alternate embodiment of an air freshener 60 is shown. In this alternate embodiment, a core 62 still includes an upstanding inner wall 18 separated from an I-beam strength section 22 (not shown in FIGS. 9 to 14) by a second trough 24. However, rather than the inside exterior wall and first trough as shown in the embodiment in FIG. 1, this second embodiment 60 includes an inner section 68 between the upstanding inner wall 18 and the third trough 34. The inner section 68 comprises the same polymer material of the remainder of the core. A series of slots 64 are formed in or cut from the inner section 68 forming an array of slots 64 separated by ribs 66. The slots 64 are disposed in a direction generally perpendicular to the center axis of the core 62. The slots 64 and ribs 66 enhance bending or twisting of the air freshener 60 when opening the air freshener by moving the proximal end 14 and distal end 16 away from one another, such as in direction(s) generally parallel to the axis 40 of the air freshener 60 or generally along the central axis of the air freshener.

In the preferred embodiments, the air freshener 10, 60 of the invention may generally have a thickness of about 1 cm, and a length of about 8 to 10 cm (as measured from the ends to the apex of the curved or rounded clip). The I-beam strength section has a length traversing the length of the core, and generally about 16 to 20 cm. The width of the "I" portion of the I-beam strength section is about 3 to 5 mm. The upstanding inner wall has a thickness of about 1 to 2 mm. The depth of the first trough is about 5 to 8 mm. The depth of the second trough is about 4 to 6 mm. The depth of the third trough is about 4 to 6 mm. The length of the straps is about 1 to 2 mm, the holes defined between the ends and the straps and the I-beam strength section have lengths of about 5 mm and heights of about 1 to 2 mm.

Figure 16:
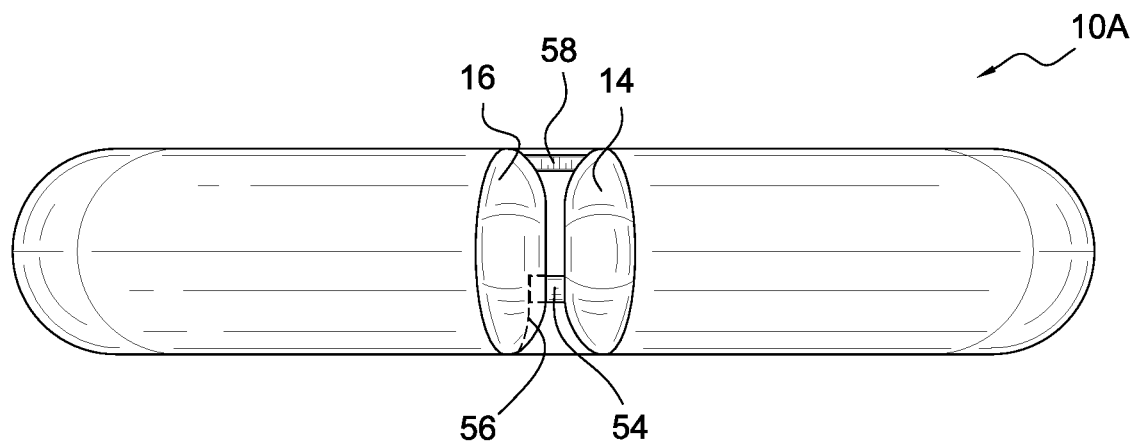
FIG. 16 is a bottom view of an air freshener with a strap and with male and female connectors.
Figure 17:
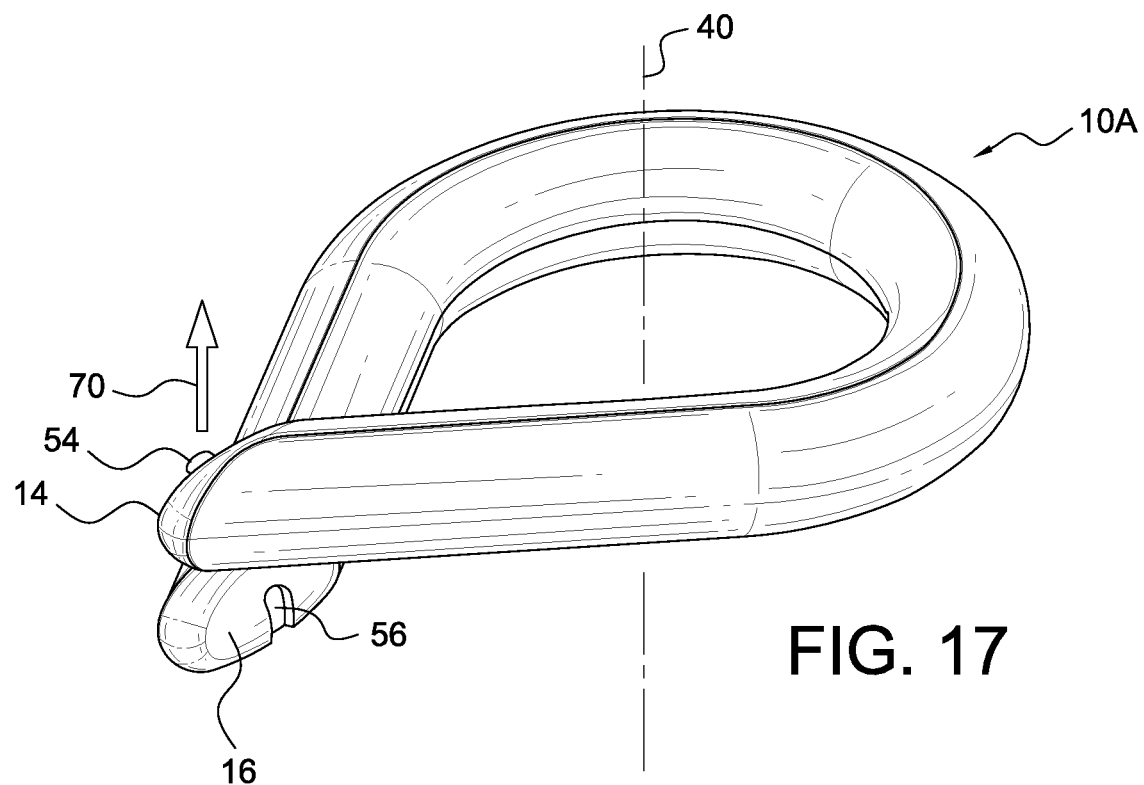
FIG. 17 is a right rear perspective view of the air freshener of FIG. 16 with flexed apart distal end and proximal end.

FIGS. 16 and 17 show an air freshener 10A comparable to that shown in FIGS. 1-8 that includes additional features at or near the proximal end 14 and distal end 16. In FIG. 16, a strap 58 links the proximal end 14 and the distal end 16 together. The strap 58 may be formed from the same polymeric material as the core 12 when the core is molded. The strap 58 helps maintain alignment during molding and curing of the air freshener. For example, the strap 58 helps to resist twisting, bending and/or separating of the proximal end and distal end. The strap 58 may have a thin profile such that a user or consumer may snap, break or cut the strap before installing the air freshener 10A onto a mounting structure or receiving structure. Once the strap 58 is broken, the proximal end 14 and distal end 16 may be separated from one another or moved away from one another.

As shown in FIG. 17, the proximal end 14 and distal end 16 may be flexed away from one another, such as in the direction of arrow 70. By twisting or flexing or pulling apart the ends 14, 16 of the air freshener 10A, 60, the air freshener may be opened to permit it to be installed over or around mounting structures or receiving structures. Representative mounting structures or receiving structures include, but are not limited to, the supporting post or neck of a rear view mirror of a motor vehicle, or a door handle, or a curtain rod, or a furniture or cabinet handle or drawer pull, or a clothes rack or closet rod, or a shoe, or a shoe rack, or a laundry hamper, or a gym bag, or a locker, or a shower door, or a trash can, or a pipe or wire, or a table or a cart. Upon releasing the twisting, flexing or pulling force, the ends 14, 16 preferably return substantially to their unflexed or closed configuration. In such manner, the air freshener 10A readily may be installed over or around a mounting or receiving structure.

Twisting, flexing or pulling apart of the ends 14, 16 of the air freshener 10A, 60 is enhanced where the core and the fragranced polymer are formed of different polymers that do not chemically bind or adhere to one another. Some slippage between the polymers of the core and the fragranced polymer permits optimum bending to an open configuration and recovery or return to a closed configuration or substantially closed configuration.

In one embodiment shown in FIGS. 16 and 17, the face surfaces 36, 38 of the proximal end 14 and distal end 16 of the air freshener 10A may be connected together when the air freshener 10A is installed or engaged to a mounting structure. In such embodiment, for example, a male connector 54 may project from the face surface of either the proximal end or the distal end, and a female receiving channel or orifice 56 may be provided in the face surface of the other end. The male connector 54 may be held within the female receiving channel or orifice 56 when the connector is closed, and may be removably slid or ejected from the female receiving channel or orifice 56 to open the air freshener 10A.

Figure 18:
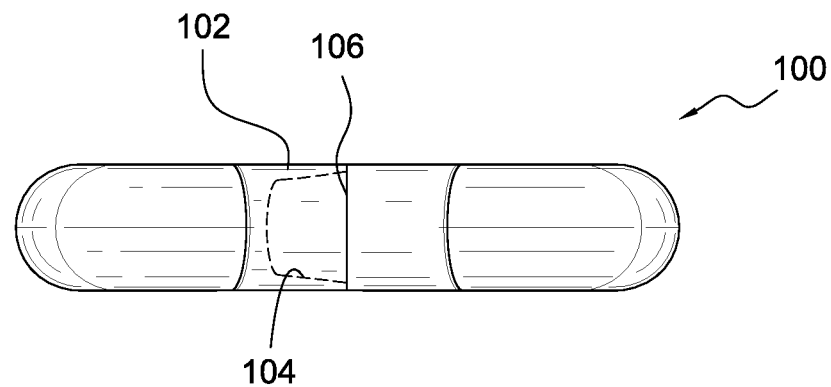
FIG. 18 is a bottom view of an alternative air freshener in a ring configuration.
Figure 19:
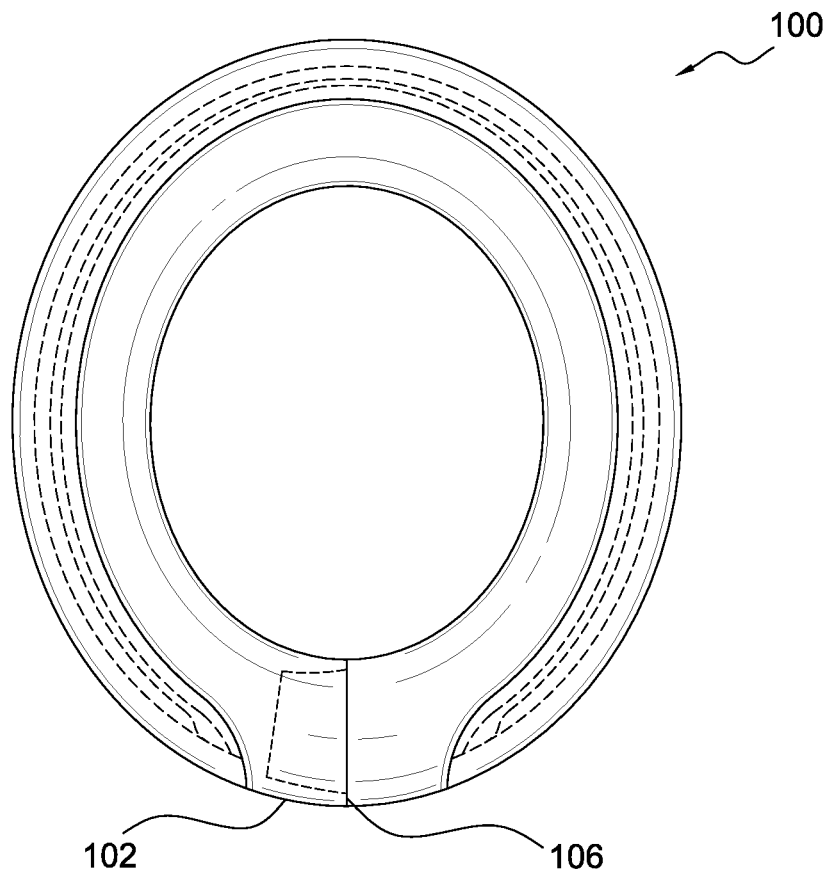
FIG. 19 is a front plan view of the air freshener of FIG. 18.

In another embodiment according to the invention shown in FIGS. 18 and 19, an air freshener 200 is shown in a closed configuration, forming a circular ring. A first or proximal end 202 of the air freshener 200 has a first outer diameter and defines in its end face an open cavity or recess 204 therein. A second or distal end 206 of the air freshener 200 has an outer diameter smaller than the first outer diameter. The second or distal end 206 mates within the cavity or recess 204 of the first or proximal end 202. To open the air freshener 200, the ends 202, 206 are pulled apart or pulled away from one another to create separation or open space between them.

Figure 20:
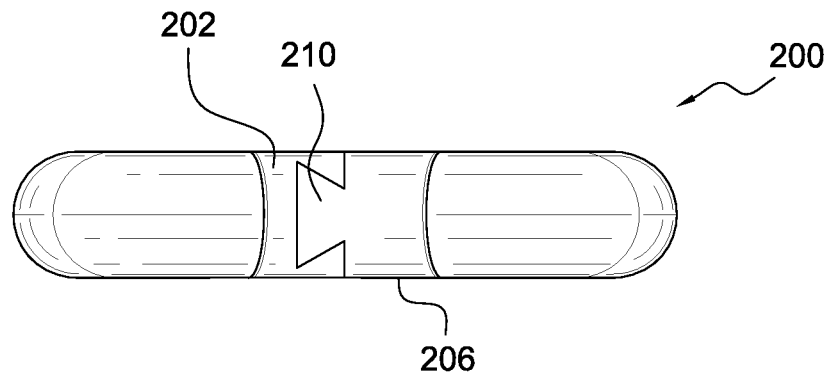
FIG. 20 is a bottom view of yet another alternative air freshener in a ring configuration.
Figure 21:
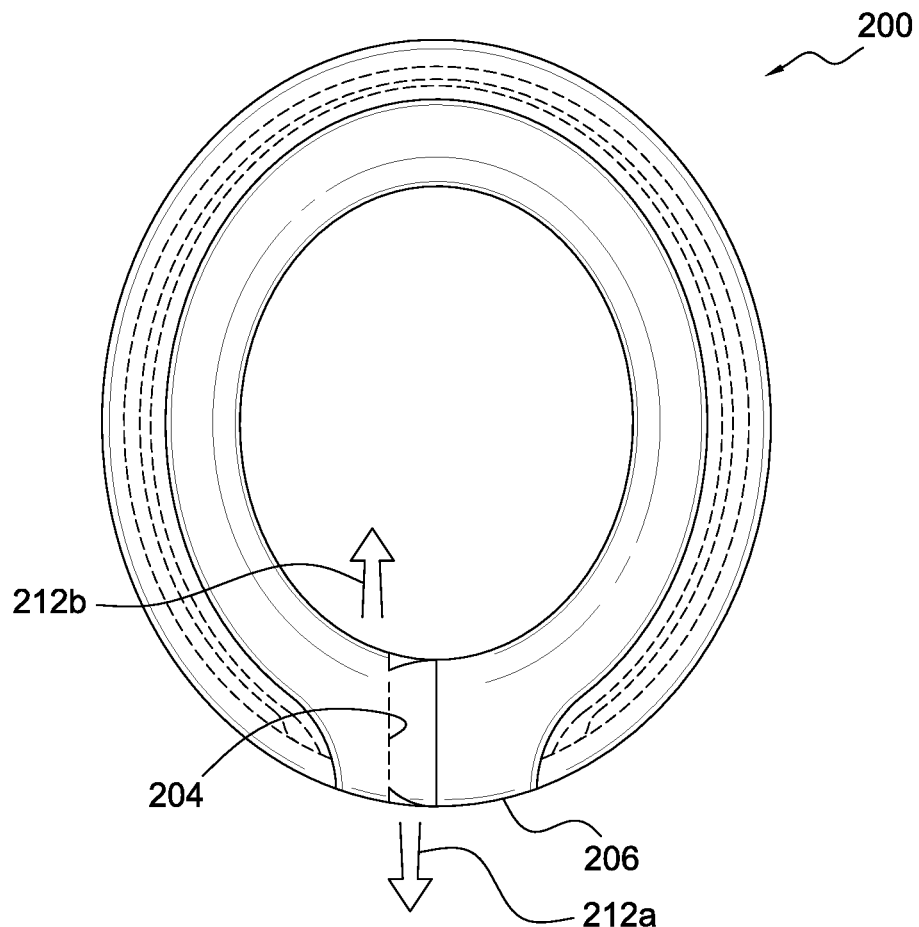
FIG. 21 is a front plan view of the air freshener of FIG. 20.

In still another embodiment according to the invention shown in FIGS. 20 and 21, an air freshener 300 forms a circular ring in closed configuration. A first or proximal end 302 of the air freshener 300 defines a recess or cavity 304. A second or distal end 306 of the air freshener 300 defines a mating extension 310 in the form of a dovetail. Such mating extension 310 releaseably slides for connection into the recess or cavity 304. To open the air freshener 300, the ends 302, 306 are slid in direction of arrows 312a, 312b to release the mating extension 310 from the mating recess or cavity 304. Once released, the ends 302, 306 may be pulled apart or pulled away from one another to create separation or open space between them.

Figure 22:
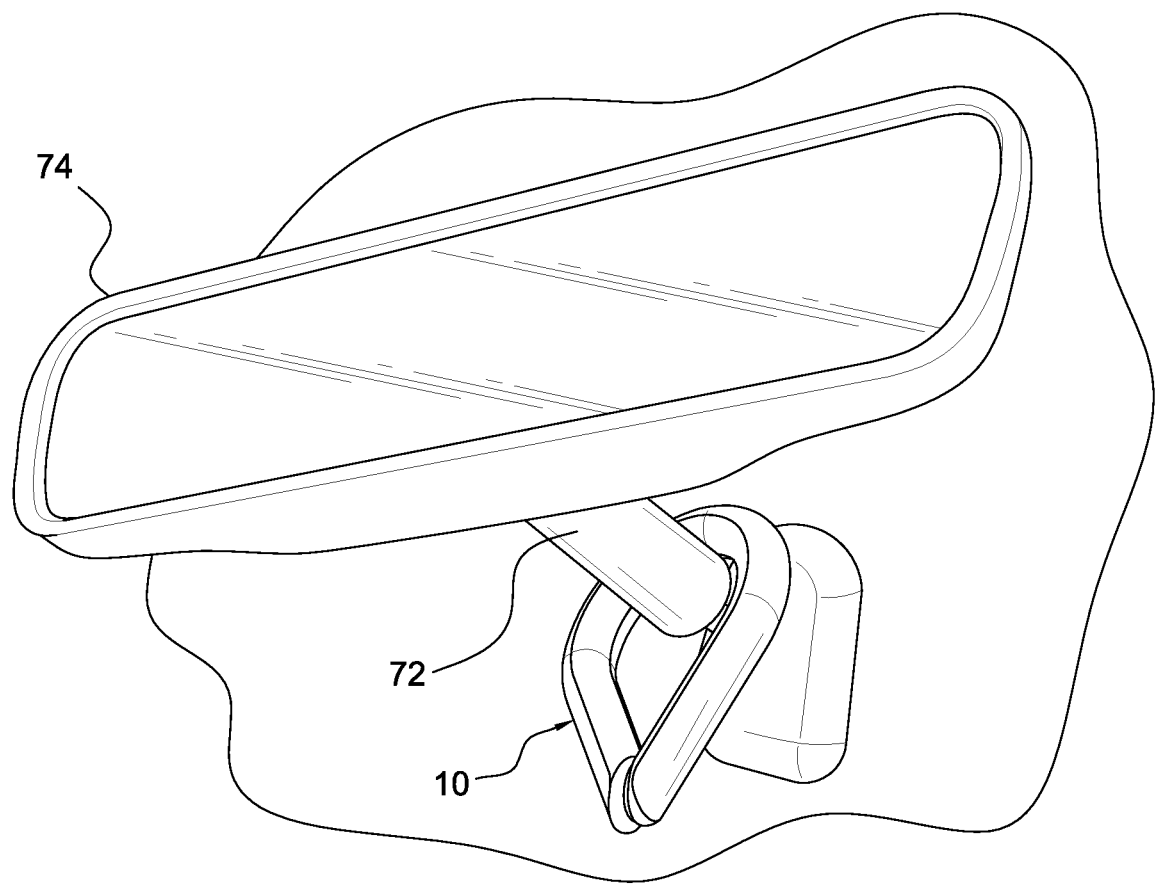
FIG. 22 is a right front perspective view of an air freshener installed on a rear view mirror support or neck.

Referring to FIG. 22, an air freshener 10 according to the invention is installed around a supporting post 72 of a rear view mirror 74 of a motor vehicle. The invention has been illustrated with particular reference to suspending or hanging the air freshener 10 to a rear view mirror of a motor vehicle. The air freshener 10 may be useful in alternative environments of use, such as attached or clipped to curtain rods in closets or cabinets, or to motor vehicle door handles, curtain rods, closet rods, hangers, shelving, shelving support posts, drawer pulls, drawer handles, belt loops, shoes, shoe racks, hampers, gym bags, lockers, shower doors, towel racks, trash cans, pipes, wires, tables, and carts, and is not intended to be limited to the environment of use illustrated here.

Alternatively, an air freshener according to the invention may be installed on a belt or on a belt loop or other clothing item and worn as a personal air freshening device. Such embodiment has particular appeal where the fragrance material comprises a volatile insecticide, or where the fragrance material comprises a cold or allergy vapor remedy.

EXAMPLE

An example air freshener is formed as a clip of the embodiment of FIGS. 1-8. The core is injection molded of about 6 g of a polypropylene copolymer. The sleeve is injection molded over the core. The sleeve comprises 5.75 g of a polyethylene copolymer, with 30 percent by weight of vanilla fragrance oil and 3 weight percent color.

Air fresheners may be tested for fragrance character and fragrance strength using a fragrance panel test known in the fragrance industry. A sample air freshener product is suspended in a room with dimensions of 25 feet by 16 feet by 9 feet. A panel of at least four persons ranks the strength and character of the aroma emitted by the various air freshener products on a scale of 0 to 5, with 5 being the strongest and 5 being the closest in character to the fragrance oil. The fragrance power and fragrance character are observed over a four-week period. The fragrance power values are averaged, and the fragrance character values are averaged. Products that receive average rankings of 3 and above for the entire testing period are satisfactory for use as continuous action room air fresheners.

Air fresheners may be tested for suitability and durability for use as air fresheners. For example, the air fresheners may be frozen for at least 12 hours and thawed over a repeated number of cycles (such as 3 cycles) to determine whether fragrance material exudes from the polymer upon thawing. Air fresheners may be heated to an elevated temperature of at least 120° F. and held for 4 weeks at such temperature, in packaging and outside of packaging, to determine whether fragrance exudes and whether fragrance strength and fragrance character degrade. Air fresheners may be exposed to ultraviolet light testing for at least 4 weeks to determine effect of light on product color and fragrance character.

While preferred embodiments of the invention have been described and illustrated here, various changes, substitutions and modifications to the described embodiments will become apparent to those of ordinary skill in the art without thereby departing from the scope and spirit of the invention.

What is claimed is:

1. An air freshener, comprising:
   a core defining a proximal end, a distal end, a length between the proximal end and distal end, an upstanding inner wall, and a central axis along the length of said core of the air freshener, wherein the air freshener encircles an axis that is substantially perpendicular to the central axis;
   an I-beam strengthening section along the length of said core, with a first hole through the I-beam strengthening section at or near the distal end of the core, and with a second hole through the I-beam strengthening section at or near the proximal end of the core, said I-beam strengthening section comprising a flange spaced apart from the upstanding inner wall of the core by a web, said web defining a first trough between the upstanding inner wall of the core and the flange on one side of said web and defining a second trough opposite and below the first trough on an opposite side of said web between the upstanding inner wall of the core and the flange;

a fragranced polymer covering the I-beam strengthening section, said fragranced polymer comprising at least one polymer incorporating one or more fragrance materials.

2. The air freshener of claim 1, wherein the upstanding inner wall begins at or near the proximal end and terminates at or near the distal end.

3. The air freshener of claim 1, wherein the I-beam strengthening section defines an apex and a reinforcement is provided at the apex.

4. The air freshener of claim 1, wherein the fragranced polymer is disposed over and around the flange and web of the I-beam strengthening section.

5. The air freshener of claim 1, wherein the fragranced polymer is disposed over the flange of the I-beam strengthening section, through the first hole and through the second hole.

6. The air freshener of claim 1, wherein the central axis is curved along at least a portion thereof.

7. The air freshener of claim 1, wherein the fragranced polymer is over-molded over the flange of the I-beam strengthening section.

8. The air freshener of claim 7, wherein the fragranced polymer forms a convexly curved outer sleeve of the air freshener.

9. The air freshener of claim 1, wherein the core has an interior section defining a plurality of ribbed channels that are disposed in a spaced apart relation in an array between a first side of the upstanding inner wall and an exterior wall.

10. The air freshener of claim 1, wherein the fragranced polymer comprises a polymer selected from the group consisting of: polyvinylchloride, polyethylene, low density polyethylene (LDPE), high density polyethylene (HDPE), thermoplastic elastomer (TPE), polypropylene, ethylene vinyl acetate, ethylene vinyl acetate copolymer, acetate, butyrate, propionate, silicone, copolymers thereof, and mixtures thereof.

11. The air freshener of claim 10, wherein the one or more fragrance materials comprise a fragrance material selected from the group consisting of: natural and synthetic fragrance oils, and mixtures thereof.

12. The air freshener of claim 1, wherein the core comprises a polymer selected from the group consisting of: polyvinylchloride, polyethylene, polyethylene terephthalate (PET), polyoxymethylene, polyamide (nylon), low density polyethylene (LDPE), high density polyethylene (HDPE), polypropylene, ethylene vinyl acetate, acrylonitrile butadiene styrene (ABS), styrene-acrylonitrile (SAN), rubber, thermoplastic elastomer (TPE), silicone, copolymers thereof, and mixtures thereof.

13. The air freshener of claim 1, wherein the proximal end terminates at a face surface, and the distal end terminates at a second face surface, and wherein the face surface of the proximal end and the second face surface of the distal end are juxtaposed in substantially facing relation to one another.

14. The air freshener of claim 13, wherein the face surface of the proximal end and the second face surface of the distal end are spaced apart from one another when the air freshener is in closed configuration.

15. The air freshener of claim 1, wherein the proximal end terminates at a face surface and the distal end terminates at a second face surface, and wherein the face surface of the proximal end and the second face surface of the distal end slidably interlock.

* * * * *